United States Patent
Tamura et al.

(10) Patent No.: US 9,281,159 B2
(45) Date of Patent: Mar. 8, 2016

(54) RADIATION GENERATING APPARATUS AND RADIOGRAPHING SYSTEM USING THE SAME

(71) Applicant: CANON KABUSHIKI KAISHA, Tokyo (JP)

(72) Inventors: Miki Tamura, Kawasaki (JP); Kazuyuki Ueda, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/349,719

(22) PCT Filed: Nov. 29, 2012

(86) PCT No.: PCT/JP2012/081586
§ 371 (c)(1),
(2) Date: Apr. 4, 2014

(87) PCT Pub. No.: WO2013/081179
PCT Pub. Date: Jun. 6, 2013

(65) Prior Publication Data
US 2014/0294150 A1 Oct. 2, 2014

(30) Foreign Application Priority Data
Dec. 2, 2011 (JP) ................................. 2011-264398

(51) Int. Cl.
*H01J 35/10* (2006.01)
*H01J 35/12* (2006.01)
(Continued)

(52) U.S. Cl.
CPC ................ *H01J 35/12* (2013.01); *G01N 23/04* (2013.01); *H05G 1/025* (2013.01); *H05G 1/04* (2013.01)

(58) Field of Classification Search
CPC .......... H01J 35/08; H01J 35/10; H01J 35/12; H01J 35/16; H05G 1/02; H05G 1/04; A61B 6/4488
USPC .................. 378/119, 121, 130, 141, 199, 200
See application file for complete search history.

(56) References Cited

U.S. PATENT DOCUMENTS

| 5,083,307 A | 1/1992 | Meinel et al. ................. 378/200 |
| 6,778,635 B1 * | 8/2004 | Richardson ........... H01J 35/106 378/130 |

(Continued)

FOREIGN PATENT DOCUMENTS

| JP | H02-077900 | 6/1990 |
| JP | 2002-025792 | 1/2002 |

OTHER PUBLICATIONS

JPO Office Action issued on Dec. 1, 2015, in counterpart Japanese patent application 2011-264398, with partial translation.

*Primary Examiner* — Courtney Thomas
(74) *Attorney, Agent, or Firm* — Fitzpatrick, Cella, Harper & Scinto

(57) ABSTRACT

In a radiation generating apparatus of the invention, a radiation tube having a cathode for emitting an electron and an anode for generating a radiation by an irradiation of the electron emitted from the cathode is enclosed in a housing container filled with an insulating liquid. The apparatus has a mechanism in which a voltage for allowing the insulating liquid to flow can be applied between the cathode and the anode in a state where the cathode does not emit any electron. Even when the generation of the radiation is stopped, the insulating liquid can be efficiently sufficiently cooled without providing mechanical stirring means, and a high reliability is obtained even for intermittent use.

11 Claims, 7 Drawing Sheets

(51) Int. Cl.
    *H05G 1/02*      (2006.01)
    *H05G 1/04*      (2006.01)
    *G01N 23/04*     (2006.01)

(56) References Cited

U.S. PATENT DOCUMENTS

| | | | |
|---|---|---|---|
| 8,472,585 B2 | 6/2013 | Ogura et al. | 378/111 |
| 8,774,364 B2 | 7/2014 | Aoki et al. | 378/104 |
| 2005/0163285 A1 | 7/2005 | Kudo | 378/144 |
| 2006/0008055 A1* | 1/2006 | Sundaram | H05G 1/025 378/119 |
| 2012/0307974 A1 | 12/2012 | Yamazaki et al. | 378/52 |
| 2012/0307978 A1 | 12/2012 | Yamazaki et al. | 378/121 |
| 2013/0016810 A1 | 1/2013 | Tamura et al. | 378/62 |
| 2013/0016811 A1 | 1/2013 | Ueda et al. | 378/62 |
| 2013/0016812 A1 | 1/2013 | Yanagisawa et al. | 378/62 |
| 2013/0034207 A1 | 2/2013 | Aoki et al. | 378/62 |
| 2013/0148781 A1 | 6/2013 | Yamazaki et al. | 378/62 |
| 2013/0230143 A1 | 9/2013 | Ueda et al. | 378/62 |
| 2013/0235975 A1 | 9/2013 | Tamura et al. | 378/62 |
| 2014/0140480 A1 | 5/2014 | Ogura et al. | 378/62 |
| 2014/0140486 A1 | 5/2014 | Yanagisawa et al. | 378/141 |
| 2014/0177800 A1 | 6/2014 | Sato et al. | 378/62 |

* cited by examiner

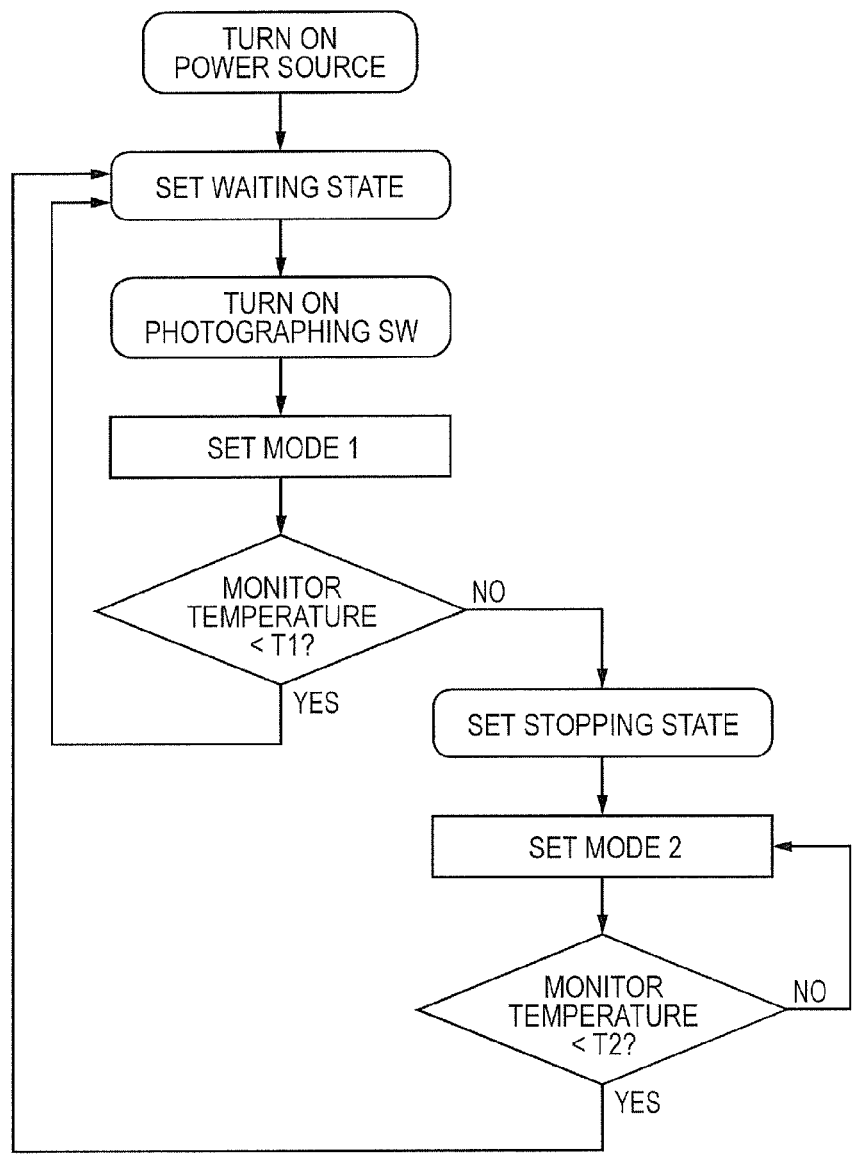

RADIATION GENERATING APPARATUS AND RADIOGRAPHING SYSTEM USING THE SAME

TECHNICAL FIELD

The invention relates to a radiation generating apparatus which can be applied to a non-destructive X-ray photographing or the like in a medical equipment field and an industrial equipment field and relates to a radiographing system using the radiation generating apparatus.

BACKGROUND ART

Generally, in a radiation generating apparatus, by applying a high voltage between a cathode and an anode arranged in a radiation tube, an electron which is emitted from the cathode is irradiated to the anode, thereby generating a radiation such as an X-ray or the like. In the radiation generating apparatus like this, in order to assure withstanding voltage performance against the high voltage and to cool the radiation tube, such a structure that the radiation tube and a high-voltage circuit board are enclosed in a container filled with an insulating liquid is used. When the electron emitted from the cathode has entered the anode, since most of the incident energy is converted into a heat, the heat generated in the anode is propagated to the insulating liquid and is radiated into the external atmosphere from the insulating liquid through the housing container.

However, in order to cool the anode by the insulating liquid and radiate the heat generated in the anode to the outside from the insulating liquid through the housing container, it is necessary that the insulating liquid flows and is stirred an the housing container. If the insulating liquid is not stirred, the heat is not sufficiently radiated, so that there is a case of occurrence of a thermal damage of the anode, decomposition/deterioration of the insulating liquid, a deterioration of electronic parts constructing the high-voltage circuit board, or the like. When the decomposition/deterioration of the insulating liquid progresses, there is a case where the withstanding voltage performance of the insulating liquid deteriorates and an electric discharge occurs in use of a long time.

Patent Literature 1 discloses an X-ray generating apparatus having a fan for allowing an insulating oil in which an X-ray tube has been sealed to be circulated in the tube container.

CITATION LIST

Patent Literature

PTL 1: Japanese Patent Application Laid-Open No. 2002-25792

SUMMARY OF INVENTION

Technical Problem

If a mechanical mechanism such as an electric fan or the like is provided in the tube container, it is difficult to realize a miniaturization and a light weight as a whole apparatus. In the case of intermittently generate the X-ray, it is necessary to sufficiently cool the insulating liquid for a period of time until the generation of the X-ray is subsequently started after the generation of the X-ray was stopped. However, for this purpose, the electric fan has to be continuously driven even after the generation of the X-ray was stopped.

Such a phenomenon that when a high voltage is applied to the insulating liquid such as an electrical insulating oil, the insulating liquid flows has been known. It is a phenomenon called an electrical hydrodynamics effect. The higher the voltage (field strength) which is applied at this time is, the higher a flowing speed of the insulating liquid is.

The inventors et al. have found out such a phenomenon that when a high voltage has been applied between the cathode and the anode even in the radiation generating apparatus, a flow of the insulating liquid due to the electrical hydrodynamics effect occurs.

According to the invention, by using the flowing phenomenon of the insulating liquid, the insulating liquid can be cooled without providing mechanical stirring means. It is an object of the invention to provide a radiation generating apparatus having a high reliability in which even when a generation of a radiation is stopped, an insulating liquid can be efficiently and sufficiently cooled, and which is suitable for intermittent use.

Solution to Problem

To solve the above problem, according to the invention, there is provided a radiation generating apparatus in which a radiation tube having a cathode for emitting an electron and an anode for generating a radiation by an irradiation of the electron emitted from the cathode is enclosed in a housing container filled with an insulating liquid, wherein the apparatus has a mechanism in which a voltage for allowing the insulating liquid to flow can be applied between the cathode and the anode in a state where the cathode does not emit any electron.

Advantageous Effects of Invention

According to the invention, the voltage for allowing the insulating liquid to flow can be applied between the cathode and the anode in the state where the cathode does not emit any electron. Therefore, even when the generation of the radiation is stopped, the insulating liquid can be stirred without providing any special stirring means. Since the special stirring means is not provided, the miniaturization and the light weight of the apparatus can be realized. When the generation of the radiation is stopped, since a temperature of the anode does not rise, the insulating liquid can be efficiently and sufficiently cooled in a short time. Thus, the decomposition/deterioration of the insulating liquid due to a thermal damage or overheat of the anode can be suppressed and the high reliability can be realized even in the intermittent use.

Further features of the present invention will become apparent from the following description of exemplary embodiments with reference to the attached drawings.

BRIEF DESCRIPTION OF DRAWINGS

FIG. 4 is a flowchart showing an example of a controlling method of the radiation generating apparatus of the invention.

DESCRIPTION OF EMBODIMENTS

Exemplary embodiments of a radiation generating apparatus of the invention will be described hereinbelow with reference to the drawings.

First Embodiment

Figure 1A:
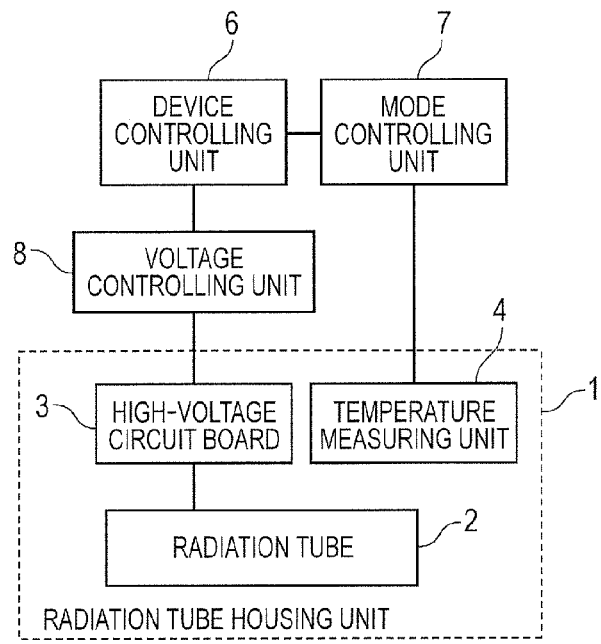
FIG. 1A is a constructional diagram illustrating an example of a radiation generating apparatus of the invention.
Figure 1B:
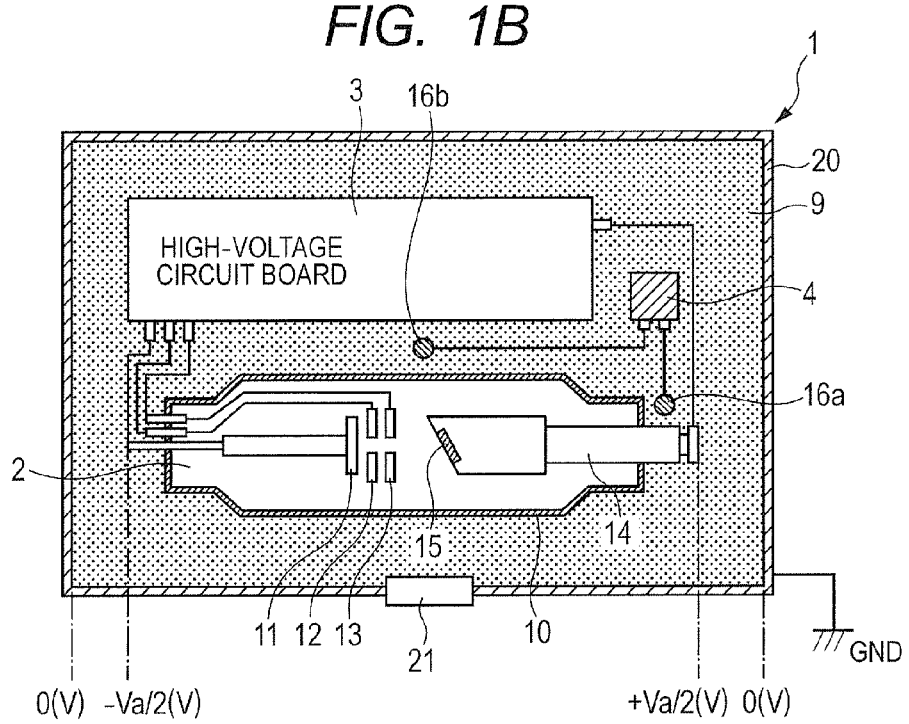
FIG. 1B is a schematic cross sectional view of a radiation tube housing unit in which a reflecting type radiation tube which is used in the radiation generating apparatus of the invention has been enclosed.

FIG. 1A is a constructional diagram of a radiation generating apparatus of the first embodiment. FIG. 1B is a schematic cross sectional view of a radiation tube housing unit 1 in FIG. 1A. In the radiation tube housing unit 1, a radiation tube 2 and a high-voltage circuit board 3 are enclosed in a housing container 20. The housing unit 1 has a radiation transmitting window 21 for extracting a radiation emitted from the radiation tube 2 to an outside. A remaining space in the housing container is filled with an insulating liquid 9.

The insulating liquid 9 has a role as a coolant of the radiation tube 2. It is desirable to use an electrical insulating oil as an insulating liquid 9. A mineral oil, a silicone oil, or the like is preferably used. As another insulating liquid 9, a fluorine electrical insulating liquid can be mentioned.

In the radiation tube 2, a cathode 11 and an anode 14 are provided in a vacuum container 10 made of glass or the like. An electron which is emitted from the cathode 11 is accelerated by a high voltage and irradiated to a target 15 formed on the surface of the anode 14, so that the radiation is emitted. In the embodiment, a reflecting type radiation tube is used as a radiation cube 2.

A hot cathode such as tungsten filament or impregnated cathode is used as a cathode 11. Tungsten, tantalum, molybdenum, or the like is used as a target 15. In the invention, as illustrated in FIG. 1B, a grid electrode 12 and a lens electrode 13 may be arranged near the cathode 11. In this case, the electron emitted in the anode direction by an electric field which is formed by the grid electrode 12 is converged by the lens electrode 13 and enters the target 15. A predetermined voltage is applied to the cathode 11, grid electrode 12, lens electrode 13, and anode 14 by the high-voltage circuit board 3.

The radiation generating apparatus of the embodiment has at least three kinds of control modes as will be described hereinafter and has a mechanism for driving the apparatus in each control mode. The control modes are switched by a mode controlling unit corresponding to the mechanism. A control signal from the mode controlling unit 7 is sent to a voltage controlling unit 8 through a device controlling unit 6. A voltage according to each control mode is applied to the cathode 11, grid electrode 12, lens electrode 13, and anode 14 by the high-voltage circuit board 3. In the invention, as illustrated in FIGS. 1A and 1B, a temperature measuring unit 4 may be provided. In FIG. 1B, temperature sensors 16a and 16b are connected to the temperature measuring unit 4. In this case, temperature signals which are measured by the temperature measuring unit 4 may be transmitted to the mode controlling unit 7 and the control modes may be switched in accordance with the temperatures which are measured by the temperature measuring unit 4.

Subsequently, each control mode of the radiation generating apparatus of the embodiment will be described by using the following Table 1. As shown in Table 1, each control mode controls the presence or absence of the emission of the electron from the cathode and the presence or absence of the applying of the high voltage between the cathode and the anode.

TABLE 1

|  | Control mode 1 Photographing mode | Control mode 2 Stirring mode | Control mode 3 Stopping mode |
| --- | --- | --- | --- |
| Electron is emitted from cathode | Yes | No | No |
| High voltage is applied between cathode and anode | Yes | Yes | No |

A control mode 1 is a photographing mode and denotes a control mode in which the electron is emitted from the cathode and the high voltage is applied between the cathode and the anode. In this case, the electron emitted from the cathode enters the anode and the radiation is emitted. At this time, since the high voltage is applied between the cathode and the anode, a high field strength portion occurs in the housing container 20 and a flow of the insulating liquid 9 occurs by the electrical hydrodynamics effect. Thus, the insulating liquid 9 in the housing container 20 is stirred.

A control mode 2 is a stirring mode and denotes a control mode serving as a feature of the invention. The control mode 2 denotes a control mode in which the high voltage is applied between the cathode and the anode in a state where no electron is emitted from the cathode. In this case, since no electron is emitted from the cathode, no radiation is emitted and a temperature of the anode does not rise either. On the other hand, since the high voltage is applied between the cathode and the anode, a flow of the insulating liquid 9 occurs by the electrical hydrodynamics effect and a state where the insulating liquid 9 is stirred is obtained. The control mode 2 is desirably used, for example, in the case where it is intended to eliminate a local temperature increase of the insulating liquid 9, the case where it is intended to promote the cooling of the radiation tube 2 and the insulating liquid 9, or the like.

A control mode 3 is a stopping mode and denotes a control mode in which no electron is emitted from the cathode and the high voltage is not applied between the cathode and the anode either.

Figure 2A:
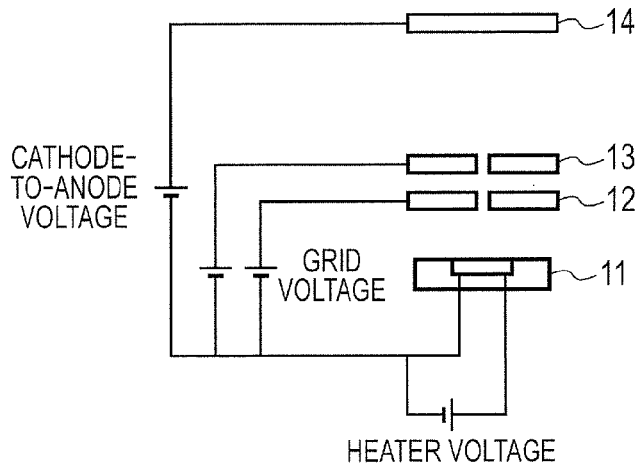
FIGS. 2A, 2B, and 2C are diagrams for describing a voltage applying method in each control mode for controlling the radiation generating apparatus of the invention.
Figure 2B:
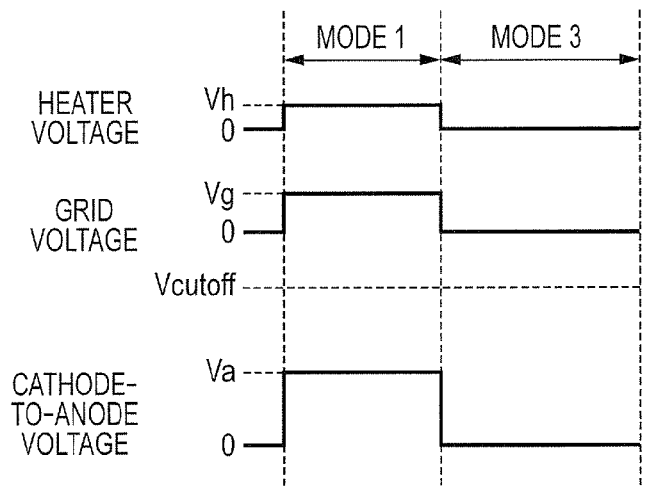
Figure 2C:
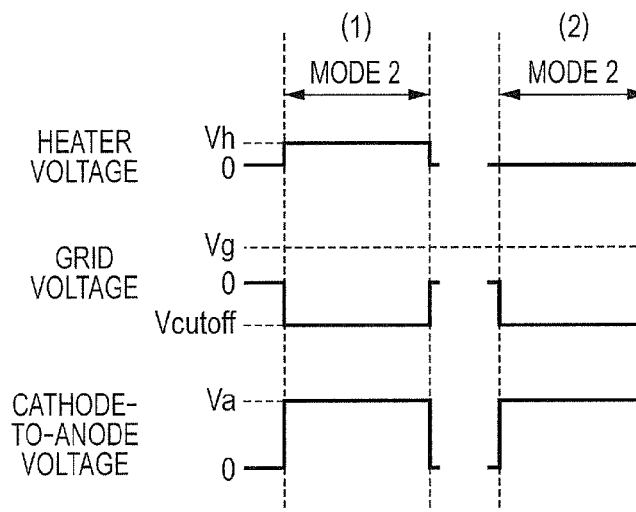

Subsequently, a voltage applying method in each control mode will be described by using FIGS. 2A, 2B, and 2C. FIG. 2A is a diagram illustrating a voltage portion regarding each control mode. FIGS. 2B and 2C are diagrams illustrating the voltage applying method in each control mode.

In FIGS. 2A to 2C, a heater voltage is a voltage which is applied to the hot cathode constructing the cathode 11. By applying a predetermined voltage Vh, a state where the electron can be emitted from the cathode 11 is obtained. An electric potential on a negative electrode side of the heater voltage is set to an electric potential of the cathode and is used as a reference potential. A grid voltage is a voltage between the grid electrode 12 and the cathode 11. By applying a predetermined voltage Vg, the electron is pulled out in the anode direction. However, at a voltage which is equal to or lower than a cut-off voltage (Vcutoff), a state where the electron is not emitted in the anode direction is obtained. A cathode-to-anode voltage is a voltage which is applied between the cathode 11 and the anode 14.

FIG. 2B is a diagram illustrating the applying voltage in the control modes 1 and 3. In the control mode 1, the heater voltage is set to Vh[V], the grid voltage is set to Vg[V], and the cathode-to-anode voltage is set to Va[V], respectively. Thus, the electron is emitted from the cathode and enters the anode, and the radiation is emitted. In the control mode 3, all of those voltages are equal to 0[V].

FIG. 2C is a diagram illustrating the applying voltage in the control mode 2. As a voltage applying method in the control mode 2, either the method (1) or (2) shown in FIG. 2C can be used. (1) is a method whereby the grid voltage is set to the cut-off voltage in a state where the heater voltage has been applied. At this time, the electric potential of the grid is lower than that of the cathode. (2) is a method whereby the heater voltage is set to 0[V] and the grid voltage is set to the cut-off voltage. By setting the heater voltage to 0V, a state where no thermion is emitted from the cathode is obtained. Further, by seeding the grid voltage to the cut-off voltage, a motion of remaining thermions in the anode direction is stopped. In both methods, the cathode-to-anode voltage is set to Va[V]. The cathode-to-anode voltage in the control mode 2 may be higher than that in the control mode 1.

Although there are an anode grounded method and a middle-point grounded method as an applying method of the cathode-to-anode voltage Va, it is desirable to use the middle-point grounded method. The anode grounded method is a method whereby when the cathode-to-anode voltage is set to Va[V], the electric potential of the anode is set to 0[V] (Gnd) and the electric potential of the cathode is set so −Va[V]. The middle-point grounded method is a method whereby the electric potential of the anode is set to +(Va−α) [V] and the electric potential of she cathode is set to −α[V]. α denotes an arbitrary value which satisfies Va>α>0 and is generally equal to Va/2.

FIG. 1B shows the electric potential of each portion in the case of the middle-point grounded method. Although it is desirable to set she cathode-to-anode voltage Va to about 40 kV to 150 kV, even if Va is equal to a high voltage out of such a range, the insulating liquid 9 can be made to flow. If the cathode-to-anode voltage Va is set to about 40 to 150 kV and the middle-point grounded method is used, a high field strength portion of about $10^6$V/m to $10^7$V/m occurs even between the cathode and the housing container and between the anode and the housing container besides the case where it occurs between the cathode and the anode. If the insulating liquid 9 exists in such a high electric field, a flow of the insulating liquid 9 occurs by the electrical hydrodynamics effect. Although a flowing speed of the insulating liquid 9 at this time depends on the voltage which is applied, shapes of the cathode and the anode, a material forming the insulating liquid 9, or the like, it is equal to about a few to hundreds of mm/sec. By such a flow of the insulating liquid 9, the insulating liquid 9 is stirred in the housing container 20. In the case of the middle-point grounded method, since the high field strength portion exists near the anode 14 of a high temperature and the flow of the insulating liquid 9 occurs near the anode 14, the cooling of the anode 14 is further promoted.

Second Embodiment

Figure 3:
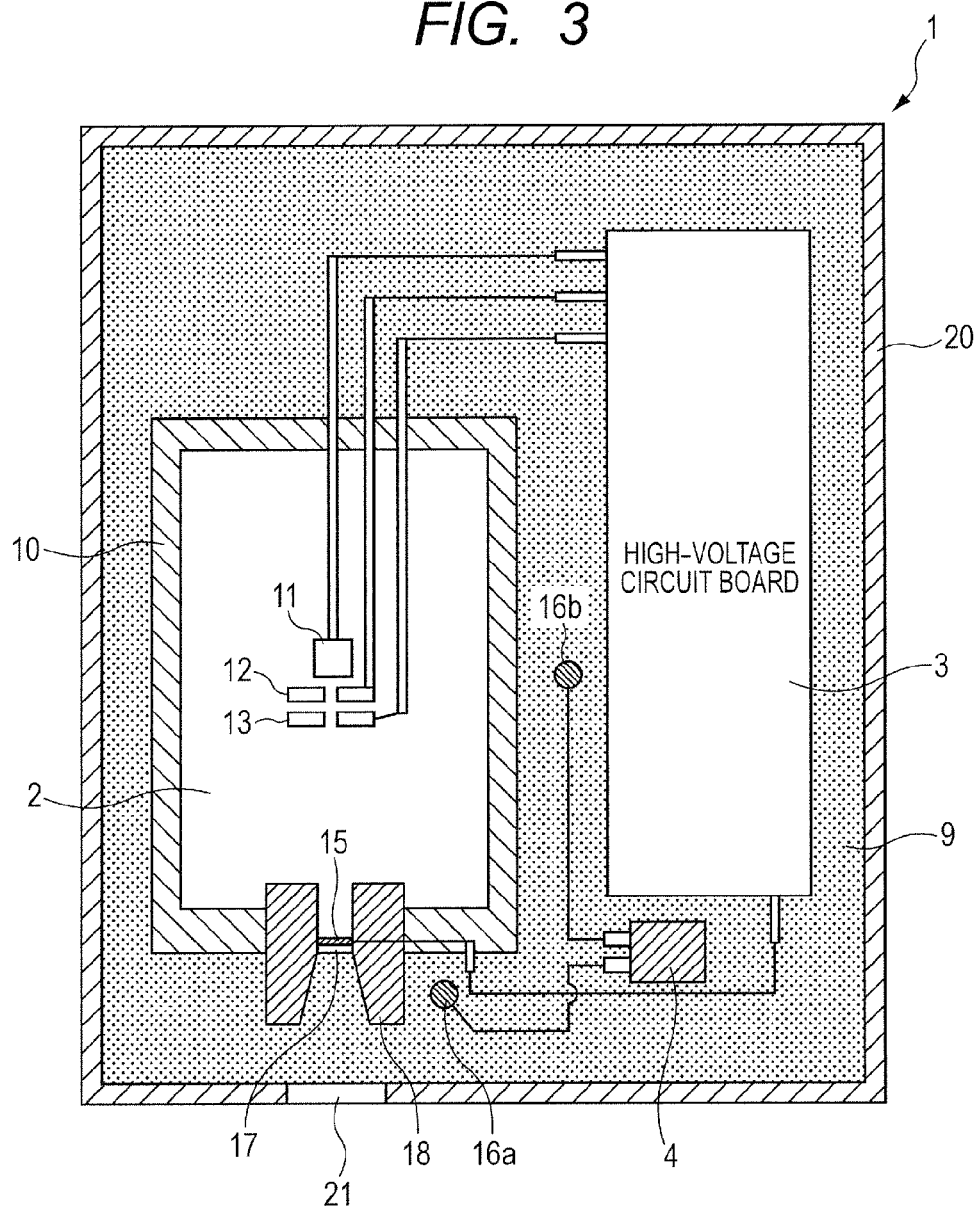
FIG. 3 is a schematic cross sectional view of the radiation tube housing unit in which a transmitting type radiation tube which is used in the radiation generating apparatus of the invention has been enclosed.

Subsequently, another example of the radiation generating apparatus of the invention will be described by using FIG. 3. FIG. 3 is a schematic cross sectional view of the radiation tube housing unit 1 which can be applied to the radiation generating apparatus of the invention. In the embodiment, a transmitting type radiation tube is used in the radiation tube 2 and other portions can be constructed in a manner similar to those in the first embodiment. The embodiment is characterized by the driving in the stirring mode in a manner similar to the first embodiment. In FIG. 3, the same members as those in FIG. 1B are designated by the same reference numerals, 11 denotes the cathode, and 15 indicates the target. The target 15 is formed on the surface of a supporting board 17. A radiation emitted from the target 15 passes through the supporting board 17 and is emitted to she outside of the radiation tube 2. In the embodiment, the target 15 plays a role of the anode. A hot cathode such as tungsten filament or impregnated cathode or a cold cathode such as carbon nanotube or the like can be used as a cathode 11. In the invention, as illustrated in FIG. 3, the grid electrode 12 and the lens electrode 13 may be arranged near the cathode 11. Tungsten, tantalum, molybdenum, or the like can be used as a target 15. Diamond, silicon nitride, aluminum nitride, or the like can be used as a supporting board 17.

A radiation shielding member 18 is provided near the target 15. The radiation shielding member 18 shields unnecessary radiation in the radiation emitted from the target 15. The electron emitted from the target 15 passes through a passage of the radiation shielding member 18 and is irradiated onto the target 15. The unnecessary radiation scattered to the cathode side of the target 15 at this time is shielded by the radiation shielding member 18. The radiation which has passed through the supporting board 17 passes through the passage of the radiation shielding member 18 and the unnecessary radiation is shielded by the radiation shielding member 18. For example, a metal material such as tungsten, tantalum, or the like can be used as a radiation shielding member 18.

Third Embodiment

Subsequently, a controlling method of the radiation generating apparatus of the invention will be described by using FIG. 4. The radiation generating apparatus of the first or second embodiment can be applied to the radiation generating apparatus. The embodiment relates to the controlling method which can be applied at the time of radiographing. FIG. 4 is a flowchart showing the controlling method.

First, when a photographing switch is pressed in a waiting state after a power source of the apparatus was turned on, a photographing mode (mode 1) is set and the photographing is started. The photographing is executed only for a preset time. After completion of the photographing, a temperature of a predetermined location in the housing container 20 is measured by the temperature measuring unit 4. If the temperature is lower than a predetermined temperature T1, the apparatus is returned to the waiting state. The waiting state is a state where although a power source circuit of the whole system is in an operating state, no voltage is output. If the temperature is equal to or higher than T1, the apparatus is set to a photographing stopping state and the operating mode is switched from the photographing mode (mode 1) to a stirring mode (mode 2). In the stirring mode (mode 2), the temperature of the predetermined location is similarly measured. If the temperature is equal to or higher than a predetermined temperature T2, the stirring mode (mode 2) is continued. If the temperature is lower than T2, the apparatus enters the waiting state.

The location where the temperature is measured can be set to a location like, for example, a temperature sensor 16a in FIG. 1B, by which the temperature of the insulating liquid 9 near the anode is measured. In this case, T1 can be set to a temperature which is lower than, for example, a heat resisting temperature (decomposition starting temperature) of the insulating liquid 9 by about tens of° C., On the other hand, the location where the temperature is measured can be set to a location like, for example, a temperature sensor 16b in FIG.

1B, by which the temperature of the insulating liquid 9 near the high-voltage circuit board 3 is measured. In this case, T1 can be set to a temperature which is lower than an upper limit temperature which is decided on the basis of temperature characteristics, heat resisting temperature, and the like of electronic parts of the high-voltage circuit board 3 by about tens of ° C. T2 can be set to a temperature which is lower than T1 by about tens of ° C. A plurality of combinations of temperature sensors and T1 and T2 may be set. The location of the temperature sensor and T1 and T2 are not limited to them.

The voltage Va which is applied between the cathode and the anode in the photographing mode (mode 1) and that in the stirring mode (mode 2) may be identical or different. The voltage Va in the photographing mode (mode 1) is set in accordance with photographing conditions. In the stirring mode (mode 2), in order to set a stirring speed, of the insulating liquid 9 to a value as large as possible, it is desirable to set the voltage Va to a value as high as possible within a range which can be set. Now, assuming that a set upper limit value of the voltage Va which is set on the basis of the withstanding voltage performance is set to Vamax, a value which is equal to or larger than 0.7×Vamax is desirable and a value which is equal to or larger than 0/8×Vamax is much desirable. For example, in the general radiation generating apparatus, since the set upper limit value of the voltage Va is equal to about 100 kV to 120 kV, it is desirable to set the voltage Va to a value which is equal to or larger than about 70 kV to 85 kV and a value which is equal to or larger than 80 kV to 95 kV or more is much desirable.

In the stirring mode (mode 2), since the insulating liquid 9 can be stirred at a high speed in a state where no electron enters the anode 14, that is, a state where the temperature of the anode 14 does not rise, the anode 14 and the insulating liquid 9 can be promptly cooled. When the target is photographed at the relatively low voltage Va, there is a case where the flowing speed of the insulating liquid 9 is low and the temperature of the insulating liquid 9 rises locally near the anode 14. However, in such a case, it is sufficient to apply the higher voltage Va in the stirring mode (mode 2). By this method, the insulating liquid 9 can be stirred at a high speed and the local temperature increase can be eliminated.

According to the controlling method of the embodiment, since the insulating liquid can be efficiently and sufficiently cooled for a short time in the stirring mode for a radiographing stopping period, even in the case where the photographing stopping period is provided between the photographing and the photographing and the photographing is intermittently performed, the radiographing having excellent reliability can be realized.

Fourth Embodiment

Figure 5A:
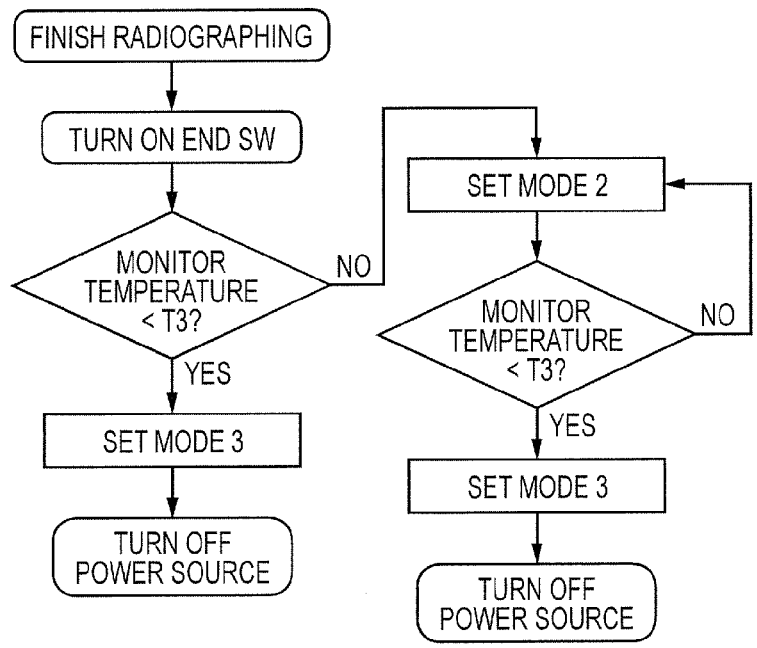
FIGS. 5A, 5B, and 5C are flowcharts showing another example of the controlling method of the radiation generating apparatus of the invention.
Figure 5B:
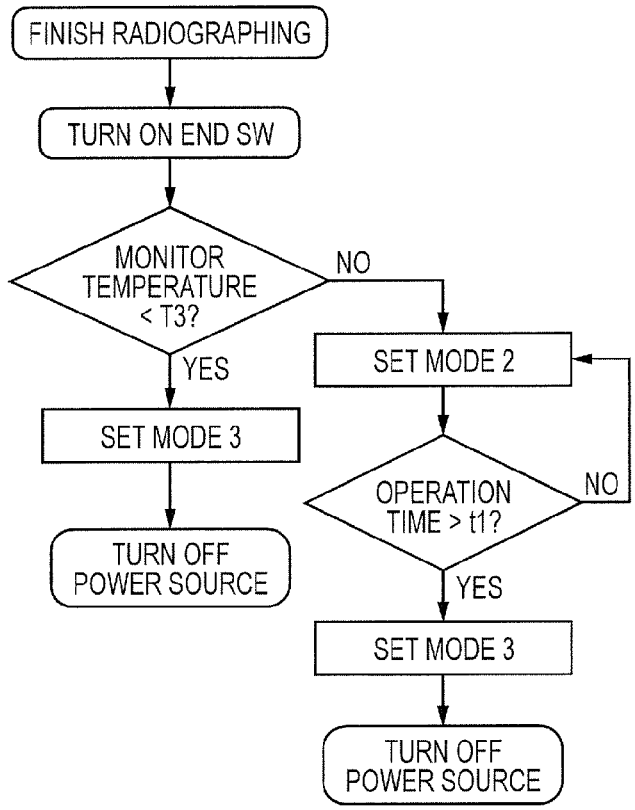
Figure 5C:
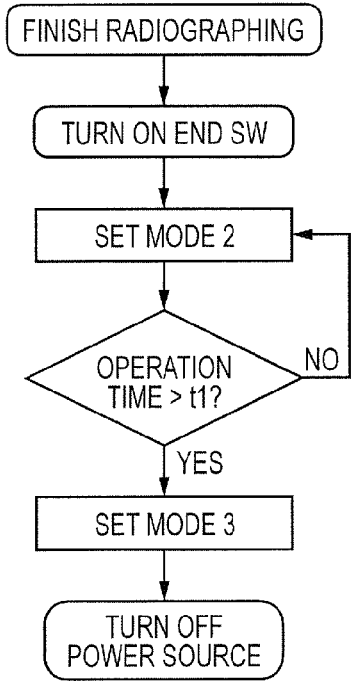

Subsequently, another controlling method of the radiation generating apparatus of the invention will be described by using FIGS. 5A, 5B, and 5C. The radiation generating apparatus of the first or second embodiment can be applied to the radiation generating apparatus. The embodiment relates to the controlling method which can be applied after the radiographing was finished. FIGS. 5A to 5C are flowcharts showing an example of the controlling method.

In FIG. 5A, first, when an end switch is pressed after the radiographing was finished, a temperature of a predetermined location in the housing container 20 is measured by the temperature measuring unit 4. If the temperature is lower than a predetermined temperature T3, the mode is shifted to a stopping mode (mode 3) and the power source of the apparatus is turned off. If the temperature is equal to or higher than T3, the mode is shifted to the stirring mode (mode 2). In the stirring mode (mode 2), the temperature of the predetermined location is similarly measured. If the temperature is equal to or higher than T3, the stirring mode (mode 2) is continued. If the temperature is lower than T3, the mode is shitted to the stopping mode (mode 3) and the power source of the apparatus is turned off. The location where the temperature is measured can be set to a location like, for example, the temperature sensor 16a in FIG. 1B, by which the temperature of the insulating liquid 9 near the anode is measured. In this case, T3 can be set to a temperature which is lower than, for example, the heat resisting temperature (decomposition starting temperature) of the insulating liquid 9 by about tens of ° C. The location where the temperature is measured can be set to a location like, for example, the temperature sensor 16b in FIG. 1B, by which the temperature of the insulating liquid 9 near the high-voltage circuit board 3 is measured. In this case, T3 can be set to a temperature which is lower than the upper limit temperature which is decided on the basis of the temperature characteristics, heat resisting temperature, and the like of the electronic parts of the high-voltage circuit board 3 by about tens of ° C. The locations of the temperature sensors and T3 are not limited to them.

In FIG. 5B, in a manner similar to FIG. 5A, if the temperature of the predetermined location is equal to or higher than T3, the mode is shifted to the stirring mode (mode 2) and the stirring mode (mode 2) is executed for a predetermined time t1. After that, the mode is shifted to the stopping mode (mode 3) and the power-source of the apparatus is turned off. In FIG. 5C, after the radiographing was finished, the stirring mode (mode 2) is executed for the predetermined time t1. After that, the mode is shifted to the stopping mode (mode 3) and the power source of the apparatus is turned off. Although t1 can be properly set in accordance with using conditions or the like, it is sufficient that t1 is set to a time necessary to reduce the temperature of the insulating liquid 9 by about tens of ° C. t1 can be set to a value within a range from about tens of seconds to a few minutes.

According to the controlling method of the embodiment, since the insulating liquid can be efficiently and sufficiently cooled for a short time in the stirring mode after the radiographing was finished, a waiting time until the next radiographing can be shortened and the radiographing having excellent reliability can be realized even at the time of the next radiographing.

Fifth Embodiment

Figure 6A:
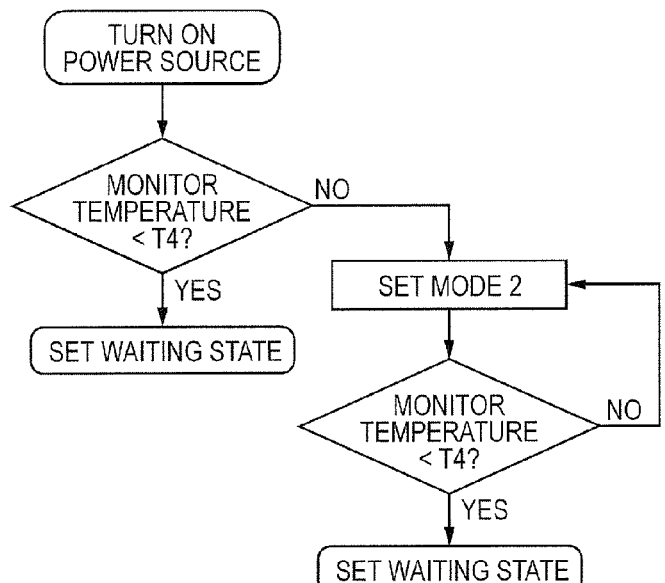
FIGS. 6A, 6B, and 6C are flowcharts showing another example of the controlling method of the radiation generating apparatus of the invention.
Figure 6B:
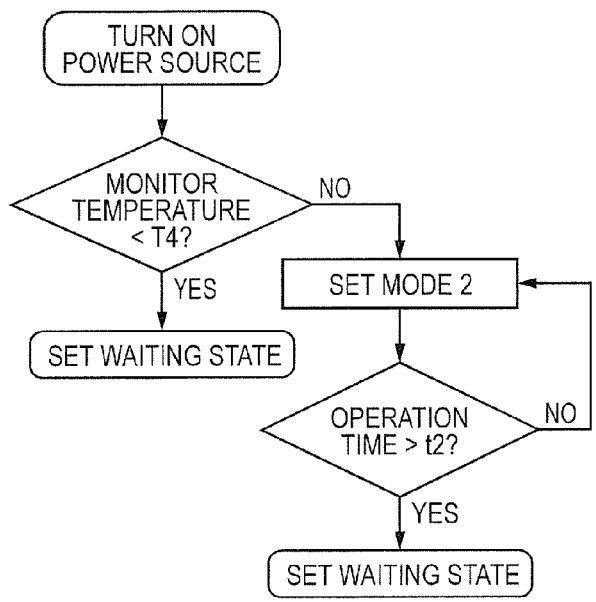
Figure 6C:
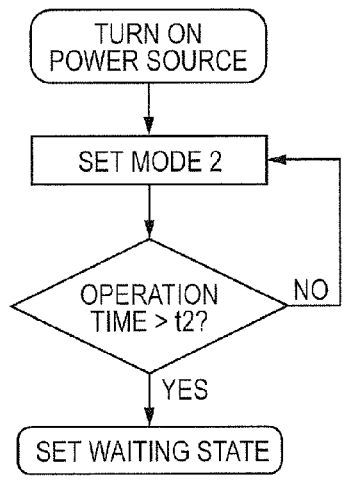

Subsequently, another controlling method of the radiation generating apparatus of the invention will be described by using FIGS. 6A, 6E, and 6C. The radiation generating apparatus of the first or second embodiment can be applied to the radiation generating apparatus. The embodiment relates to the controlling method which can be applied before the radiographing is started. FIGS. 6A to 6C are flowcharts showing an example of the controlling method.

In FIG. 6A, first, after the power source of the apparatus was turned on (after the apparatus was activated), the temperature of the predetermined location in the housing container 20 is measured by the temperature measuring unit 4. If the temperature is lower than T4, the apparatus enters the waiting state. If the temperature is equal to or higher than T4, the mode is shifted to the stirring mode (mode 2). In the stirring mode (mode 2), the temperature of the predetermined location is similarly measured. If the temperature is equal to or higher than T4, the stirring mode (mode 2) is continued. If the temperature is lower than T4, the apparatus enters the waiting state. The location where the temperature is measured can be set to the location like, for example, the temperature sensor 16a in FIG. 1B, by which the temperature of the insulating liquid 9 near the anode is measured. In this case, T4 can be set to a temperature which is lower than, for example, the heat resisting temperature (decomposition starting temperature) of the insulating liquid 9 by about tens of ° C. The location where the temperature is measured can be set to the location like, for example, the temperature sensor 16b in FIG. 1B, by which the temperature of the insulating liquid 9 near the high-voltage circuit board 3 is measured. In this case, T4 can be set to a temperature which is lower than the upper limit temperature which is decided on the basis of the temperature characteristics, heat resisting temperature, and the like of the electronic parts of the high-voltage circuit board 3 by about tens of ° C. The locations of the temperature sensors and T4 are not limited to them.

In FIG. 6B, in a manner similar to FIG. 6a, if the temperature of the predetermined location is equal to or higher than T4, the mode is shifted to the stirring mode (mode 2) and the stirring mode (mode 2) is executed for a predetermined time t2. After that, the apparatus enters the waiting state. In FIG. 6C, after the power source of the apparatus was turned on, the stirring mode (mode 2) is executed for the predetermined time t2, After that, the apparatus enters the waiting state. Although t2 can be properly set in accordance with using conditions or the like, it is sufficient that t2 is set to a time necessary to sufficiently stir the insulating liquid 9 or to reduce the temperature of the insulating liquid 9 by about tens of ° C. Here, t1 can be set to a value within a range from about tens of seconds to a few minutes.

According to the controlling method of the embodiment, since the insulating liquid can be efficiently and sufficiently cooled for a short time in the stirring mode before the radiographing is performed, such a risk that the photographing is interrupted by the increase in temperature of the insulating liquid upon photographing (or the local temperature increase) can be reduced.

The controlling method of the radiation generating apparatus in the invention may be any one of the foregoing third to fifth embodiments or may be a combination of any ones of them.

Sixth Embodiment

Figure 7:
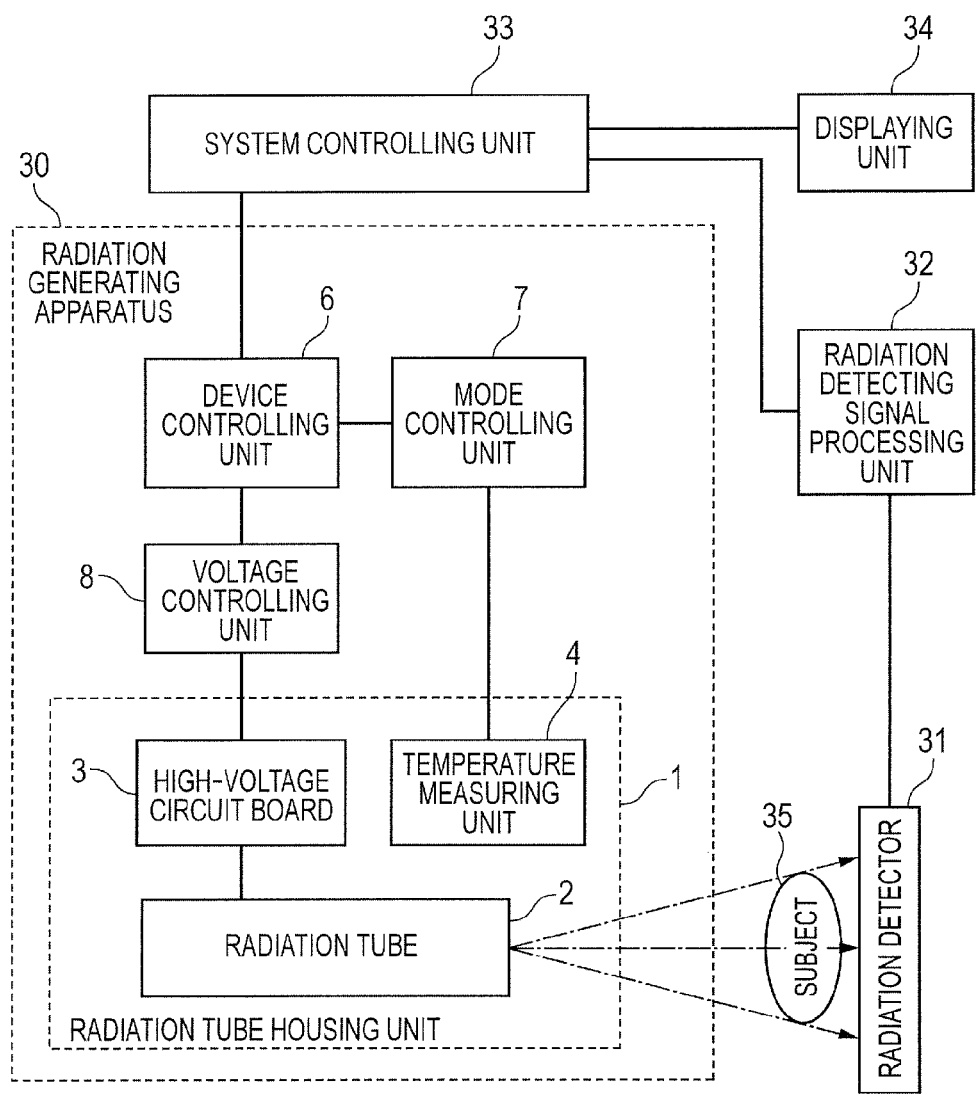
FIG. 7 is a constructional diagram of a radiographing system using the radiation generating apparatus of the invention.

Subsequently, a radiographing system using the radiation generating apparatus in the invention will be described by using FIG. 7. FIG. 7 is a constructional diagram of the radiographing system of the embodiment. The radiographing system of the embodiment has a radiation generating apparatus 30, a radiation detector 31, a radiation detecting signal processing unit 32, a system controlling unit 33, and a displaying unit 34. For example, the radiation generating apparatus of the first or second embodiment is desirably used as a radiation generating apparatus 30.

The radiation detector 31 is connected to the system controlling unit 33 through the radiation detecting signal processing unit 32. The displaying unit 34 and the device controlling unit 6 in the radiation generating apparatus 30 are connected to the system controlling unit 33.

The system controlling unit 33 controls the radiation generating apparatus 30 and the radiation detector 31 in an interlocking relational manner. For example, the system controlling unit 33 controls a voltage signal which is applied to the radiation tube 2 through the device controlling unit 6. Thus, an emitting state of the radiation from the radiation generating apparatus 30 is controlled. The radiation emitted from the radiation generating apparatus 30 is detected by the radiation detector 31 through a subject 35 and a radiation transmissive image of the subject 35 is photographed. The photographed radiation transmissive image is sent to the system controlling unit 33 through the radiation detecting signal processing unit 32 and is displayed to the displaying unit 34. The radiation generating apparatus 30 and the radiation detector 31 may be controlled in an interlocking relational manner in accordance with a target photographing image, a photographing region, or the like.

While the present invention has been described with reference to exemplary embodiments, it is to be understood that the invention is not limited to the disclosed exemplary embodiments. The scope of the following claims is to be accorded the broadcast interpretation so as to encompass all such modifications and equivalent structures and functions.

This application claims the benefit of Japanese Patent Application No. 2011-264398, filed Dec. 2, 2011, which is hereby incorporated by reference herein in its entirety.

REFERENCE SIGNS LIST

1: Radiation tube housing unit
2: Radiation tube
3: High-voltage circuit board
4: Temperature measuring unit
6: Device controlling unit
7: Mode controlling unit
8: Voltage controlling unit
9: Insulating liquid
10: Vacuum container
11: Cathode
12: Grid electrode
13: Lens electrode
14: Anode
15: Target
16a, 16b: Temperature sensor
17: Supporting board
18: Radiation shielding member
20: Housing container
21: Radiation transmitting window
30: Radiation generating apparatus
31: Radiation detector
32: Radiation detecting signal processing unit
33: System controlling unit
34: Displaying unit
35: Subject

The invention claimed is:

1. A radiation generating apparatus comprising:
    a radiation tube having a cathode for emitting an electron and an anode for generating radiation by impingement thereon of the electron emitted from said cathode;
    a housing container filled with an insulating liquid, and containing said radiation tube; and
    a mechanism in which a voltage for allowing the insulating liquid to flow is applied between said cathode and said anode in a state where said cathode does not emit any electron.

2. A radiation generating apparatus according to claim 1, wherein
    said radiation tube has a grid electrode between said cathode and said anode, and
    by controlling the voltage between said grid electrode and said cathode, said mechanism is set into a state where said cathode does not emit any electron.

3. A radiation generating apparatus according to claim 2, wherein by setting an electric potential of said grid electrode to a potential lower than an electric potential of said cathode, said mechanism is set into a state where said cathode does not emit any electron.

4. A radiation generating apparatus according to claim 2, wherein said cathode has a heater for generating a thermion, and
by setting a voltage which is applied to said heater to 0V, said mechanism is set into a state where said cathode does not emit any electron.

5. A radiation generating apparatus according claim 1, wherein said mechanism switches between: a photographing mode in which the voltage for allowing the insulating liquid to flow is applied between said cathode and said anode in a state where said cathode emits the electron; and a stirring mode in which the voltage for allowing the insulating liquid to flow is applied between said cathode and said anode in a state where said cathode does not emit any electron.

6. A radiation generating apparatus according to claim 5, wherein said mechanism drives the radiation generating apparatus in the photographing mode and switches from the photographing mode to the stirring mode in accordance with a temperature of the insulating liquid after the driving in the photographing mode has finished.

7. A radiation generating apparatus according to claim 5, wherein said mechanism drives the radiation generating apparatus in the stirring mode after the radiation generating apparatus has been activated, and switches from the stirring mode to the photographing mode in accordance with a temperature of the insulating liquid after the driving in the stirring mode has finished.

8. A radiation generating apparatus according to claim 5, wherein the voltage which is applied between said cathode and said anode in the stirring mode is higher than that in the photographing mode.

9. A radiation generating apparatus according to claim 1, wherein when it is assumed that the voltage which is applied between the cathode and the anode is equal to Va [V], the mechanism sets an electric potential of the anode to $+(Va-\alpha)$ [V] and sets an electric potential of the cathode to $-\alpha$[V] (where Va $>\alpha>0$), respectively.

10. A radiation generating apparatus according to claim 1, wherein the insulating liquid is an electrical insulating oil.

11. A radiographing system comprising:
the radiation generating apparatus according to claim 1;
a radiation detector for detecting the radiation which has been emitted from said radiation generating apparatus and has passed through a subject; and
a system controlling unit for controlling said radiation generating apparatus and said radiation detector.

\* \* \* \* \*